United States Patent [19]

Johansen et al.

[11] Patent Number: 4,806,473
[45] Date of Patent: Feb. 21, 1989

[54] PROCESS FOR ENZYMATIC PRODUCTION OF PEPTIDES

[75] Inventors: Jack T. Johansen, Rungsted Kyst; Fred Widmer, Valby, both of Denmark

[73] Assignee: De Forenede Bryggeier A/S, Copenhagen, Denmark

[21] Appl. No.: 744,308

[22] Filed: Jun. 13, 1985

Related U.S. Application Data

[60] Continuation of Ser. No. 333,292, Dec. 22, 1981, abandoned, which is a division of Ser. No. 136,661, Apr. 2, 1980, Pat. No. 4,339,534.

[30] Foreign Application Priority Data

Apr. 6, 1979 [DK] Denmark ............................. 1443/79

[51] Int. Cl.$^4$ ..................... C12P 21/04; C12P 21/02
[52] U.S. Cl. ......................................... 435/71; 435/70
[58] Field of Search .................... 435/68–71, 435/212

[56] References Cited

U.S. PATENT DOCUMENTS

| | | | |
|---|---|---|---|
| 3,276,961 | 10/1966 | Bodanszky et al. | 435/71 |
| 3,972,773 | 8/1976 | Isowa et al. | 435/70 |
| 4,086,136 | 4/1978 | Isowa et al. | 435/70 |
| 4,116,768 | 9/1978 | Isowa et al. | 435/70 |
| 4,119,493 | 10/1978 | Isowa et al. | 435/70 |
| 4,212,945 | 7/1980 | Nonaka et al. | 435/70 |
| 4,212,946 | 7/1980 | Nonaka et al. | 435/70 |

OTHER PUBLICATIONS

Widmer et al., Carlsberg Res. Commun., 44, 37–46 (1979).
Kozarich, Microbiol., 203–208 (1977).
Frère et al., FEBS Letters, 63, 112–116 (1976).
Kubota, J. Biochem., 74, 757–770 (1973).
Kritsman et al., Biokhimiya, 40(6), 1131–1134 (1975).
Hayashi et al., J. Biochem., 77, 69–79 (1975).
Johansen et al., Carlsberg Res. Commun., 41(1), 1–14 (1976).
Oka et al., Sympos. on Peptide Chem. in Japan, 79–84, Osaka (1977).

Primary Examiner—Esther M. Kepplinger

[57] ABSTRACT

A peptide having the formula $$A{-}B$$

wherein A represents an N-terminal protected amino acid residue or an optionally N-terminal protected peptide residue and B represents an optionally C-terminal protected amino acid residue, is prepared by reacting a substrate component selected from the group consisting of optionally N-terminal protected peptides of the formula $$A{-}X$$

wherein A is as defined above and X represents an amino acid with an amine component selected from the group consisting of (a) amino acids of the formula $$H{-}B{-}OH,$$

(b) optionally N-substituted amino acid amides of the formula $$H{-}B{-}NHR^3$$

wherein B is an amino acid residue and $R^3$ represents hydrogen, hydroxy, amino or alkyl, aryl or aralkyl, and (c) amino acid esters of the formula $H{-}B{-}OR^4$ or $H{-}B{-}SR^4$ wherein B is an amino acid residue and $R^4$ represents alkyl, aryl and aralkyl, in the presence of a carboxypeptidase enzyme in an aqueous solution or dispersion having a pH from 5 to 10.5, preferably at a temperature of from 30 to 50° C., to form a peptide, and subsequently cleaving a group $R^3$ or $R^4$ or an N-terminal protective group, if desired.

12 Claims, 3 Drawing Sheets

PROCESS FOR ENZYMATIC PRODUCTION OF PEPTIDES

This is a continuation of application Ser. No. 333,292, filed Dec. 22, 1981, entitled a process for enzymatic production of peptides, now abandoned which is a division of application Ser. No. 136,661, filed Apr. 2, 1980, U.S. Pat. No. 4,339,534.

BACKGROUND OF THE INVENTION

1. Field of the Invention

The present invention relates to a process for enzymatic production of peptides. More particularly, the invention relates to a process for producing peptides by using a specific group of enzymes as catalysts.

2. Description of the Prior Art

It is known to carry out syntheses of peptides by more or less sophisticated coupling reactions, both in respect of homogeneous synthesis and of heterogeneous solid phase synthesis. All these chemical methods, however, involve the risk of undesirable secondary reactions and racemizations, and it is therefore necessary to control the chemical reactions carefully to minimize or eliminate these problems. Moreover, the amino acid side chains must often be protected, requiring deblocking as the last chemical step to produce the desired peptides. Depending upon the size of the synthetized peptide, the yields may be low, and the secondary reactions frequently necessitate cumbersome purification procedures to obtain the pure peptide. All these inherent problems of chemical peptide syntheses plus the high price of several of the coupling reagents and the blocking amino acid derivatives mean that even small synthetic peptides, e.g. pentapeptides, are relatively expensive to produce.

Since enzymes are very specific catalysts, and proteolytic enzymes are thus able to hydrolyze peptide bonds in proteins, studies have previously been made of the possibilities of reversing this hydrolysis reaction or, in other words, of utilizing enzymes as catalysts in the synthesis of peptide bonds. Bergmann and Fraenkel-Conrat (ref. 1) and Bergmann and Fruton (ref. 2) made a detailed examination of this and showed in 1937 that papain and chymotrypsin could catalyze the coupling of certain acylamino acids and amino acid anilides. These studies have been continued and intensified on the basis of two fundamentally different approaches, viz. a thermodynamic and a kinetic one.

Fundamental features in the thermodynamic methods are the use of a suitable protease for catalyzing the establishment of the thermodynamic equilibrium between the reactants, and a removal of the reaction product from the reaction mixture. Thus, Isowa et al. (ref. 7-9) and U.S. Pat. No. 4,119,493 and British Pat. Nos. 1,523,546 and 1,533,129, Luisi et al. (ref. 12, 18) and Morihara (ref. 14) found that several serine, thiol and metalloendoproteases catalyze the synthesis of peptides from protected, but very easily soluble di-, tri- and tetrapeptides, provided the final products precipitate from the reaction mixture on account of their solubility being lower than the equilibrium concentration. Examples of such syntheses are illustrated in the following reaction scheme

$$Z-Leu-Phe-Phe-ODPM \quad (1)$$
ODPM = diphenyl methyl ester

$$Z-Arg(NO_2)Phe-Val-OBu^t \quad (2)$$

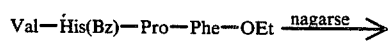
$$BOC-Val-Tyr(Bz)-Val-His(Bz)-Pro-Phe-OH \quad (3)$$

(Z = carbobenzoxy, Bz = benzoyl, BOC = tert. butyloxycarboxyl).

However, this reaction principle can only be used as general method of synthesis if, like in the conventional chemical coupling procedure, all the amino side chains with potentially ionizable groups are blocked before the reaction and deblocked after the reaction. The method is also deficient in that the high specificity of the various enzymes calls for the use of various enzymes, depending upon the type of the peptide bond to be synthetized, or rather of the amino acids forming the peptide bond. Even though these complications might be overcome, the method involves several other problems because it requires a very high concentration of enzyme (100 mg/mmole peptide), long reaction periods (1 to 3 days) and gives very varying yields (typically 20 to 80%, cf. the above mentioned U.S. and British patents).

Klibanov et al (ref. 10) have proposed to work in a system consisting of water and an organic solvent immiscible with water. This procedure, too, requires a high concentration of enzyme and a long reaction period of up to several days.

The other type of enzymatic syntheses rely on the kinetic approach of the reaction. It has been shown for most serine and thiol proteases that an acyl enzyme intermediate is formed in one of the catalytic steps during the hydrolysis of peptides or peptide esters, which is then hydrolyzed by water in the subsequent step or steps. If other nucleophiles than water are present during the hydrolysis, they too will accept the acyl group from the acyl enzyme, resulting in the formation of an amide bond. This has been studied e.g. by Fastrez and Fersht (ref. 3) who report chymotrypsin-catalyzed hydrolysis of N-acetyl-L-phenylalanine ethyl ester (Ac-Phe-OEt) in the presence of various amino acid amides. The reaction is shown in scheme (4):

Scheme (4)

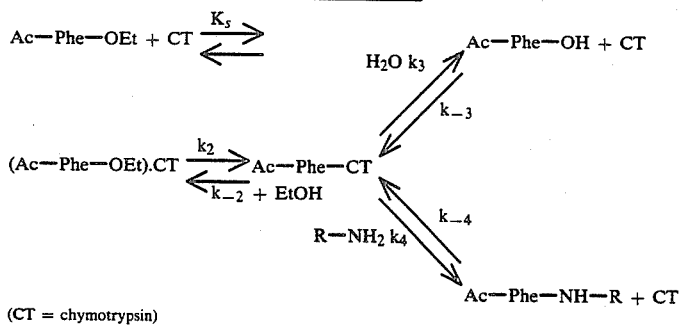

(CT = chymotrypsin)

First an enzyme substrate complex is formed followed by the formation of the acyl enzyme intermediate (Ac-Phe-CT). This is hydrolyzed by water to Ac-Phe-OH, but if a nucleophile (R-NH$_2$) is also present, the acyl enzyme intermediate will be subject to aminolysis in addition to hydrolysis. Assuming that $k_3 \gg k_{-3}$ and $k_4 \gg k_{-4}$, the ratio of aminolysis to hydrolysis clearly depends on $k_4/k_3$ as well as on the concentration of the nucleophile which is in competition with 55M water. Fastrez and Fersht found that e.g. 1M alanine amide at pH 10 is a 44 times stronger nucleophile than 55M water, which resulted in a predominant formation (larger than 95%) of the shown N-acyldipeptide-amide. Morihara and Oka (ref. 13-16) have further exploited this principle for enzymatic peptide synthesis. Using chymotrypsin and trypsin they synthetized a plurality of peptides from N-acylamino acid esters and amino acid derived nucleophiles and demonstrated that the reaction was purely kinetic since high yields could be obtained, independent of the solubility of the product.

The studies mentioned above seem to indicate that kinetic approaches possess several advantages over the thermodynamic methods:

1. Quicker reaction (in certain cases completed within few minutes).
2. Possibility of using low concentrations of enzyme.
3. Amino acid side chains must not necessarily be blocked.
4. Immobilized and insoluble enzymes may be used as the peptides are in solution, permitting automatization.

As, however, the reaction products may be soluble the synthesis must be quicker than the secondary hydrolysis of the product so that they can be separated in time.

Moreover, the known kinetic approaches are limited in their applicability because the specific properties of the enzymes examined all for the use of various enzymes for the synthesis of the various peptide bonds. Additionally, synthesis of large peptide molecules invariably causes the internal peptide bonds in the molecule to be hydrolyzed, independent of the esterolytic activity of the enzymes, due to the endopeptidase activity of the enzymes used till now.

SUMMARY OF THE INVENTION

The object of the present invention is to provide an enzymatic peptide synthesis which eliminates the drawbacks mentioned in the foregoing, and more particularly a synthesis that is of a general nature so that it is not limited to specific amino acid components, and which does not involve any risks of subsequent hydrolysis of the internal peptide bonds.

Briefly, this and other objects of the invention can be attained in a process for producing a peptide of the general formula

A—B wherein A represents an N-terminal protected amino acid residue or an optionally N-terminal protected peptide residue and B represents an optionally C-terminal protected amino acid residue, which comprises:

reacting a substrate component selected from the group consisting of
  (a) amino acid esters, peptide esters and depsipeptides of the formula A—OR$^1$ or A—SR$^1$ wherein A is as defined above and R$^1$ represents alkyl, aryl, aralkyl or an α-des-amino fragment of an amino acid residue
  (b) optionally N-substituted amino acid amides and peptide amides of the formula

A—NHR$^2$ wherein A is as defined above and R$^2$ represents hydrogen, alkyl, aryl or aralkyl, and
  (c) optionally N-terminal protected peptides of the formula

A—X wherein A is as defined above and X represents an amino acid
with an amine component selected from the group consisting of
  (a) amino acids of the formula

H—B—OH, (b) optionally N-substituted amino acid amides of the formula

H—B—NHR$^3$ wherein B is an amino acid residue and R$^3$ represents hydrogen, hydroxy, amino or alkyl, aryl or aralkyl, and
  (c) amino acid esters of the formula H—B—OR$^4$ or H—B—SR$^4$ wherein B is an amino acid residue and R$^4$ represents alkyl, aryl and aralkyl, in the presence of a carboxypeptidase enzyme in an aqueous solution or dispersion having a pH from 5 to 10.5, preferably at a temperature of from 20° to 50° C., to form a peptide, and subsequently cleaving a group $R^3$ or $R^4$ or an N-terminal protective group, if desired.

DETAILED DESCRIPTION OF THE PREFERRED EMBODIMENTS

Figure 1:
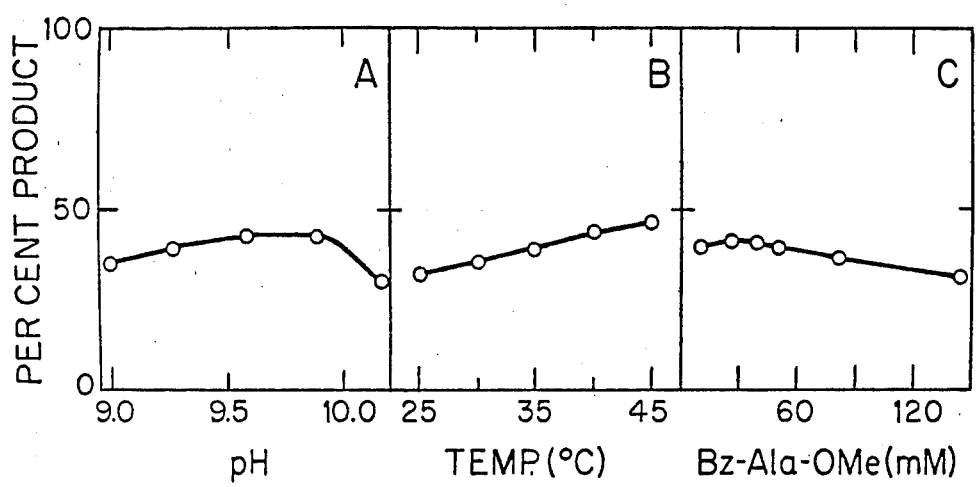
Figure 1:
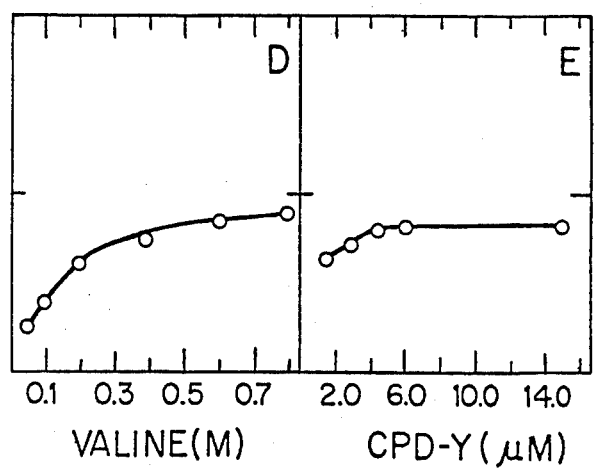

The invention is based on a fundamental change in relation to the prior art, viz. the use of exopeptidases instead of the enzymes employed till now which have all displayed predominant or at any rate significant endopeptidase activity.

It has been found that besides being exopeptidases the useful enzymes must display a peptidase activity of broad specificity to thereby allow a synthesis activity of corresponding broad specificity, which is not restricted to a single or a few types of peptide bonds. The enzymes must be capable of forming acyl enzyme intermediates of the type described above under the kinetic approaches, and must especially possess such characteristics as will allow the aminolysis of the intermediate under conditions where $k_{-4} << k_4$, cf. scheme (4) above, to avoid immediate hydrolysis of the peptides produced. The ability to form acyl enzyme intermediates may also be expressed as the ability to cleave the C-terminal protective group in the substrate component used, i.e. in the present case an esterase or amidase activity. For a synthesis to take place, said activity must dominate the peptidase activity of the enzyme under the reaction conditions used.

This multiplicity of characteristics is found in the group of exopeptidases called carboxypeptidases, which are capable of hydrolyzing peptides with free carboxyl groups. It has been found that a plurality of such carboxypeptidases exhibit different enzymatic activities which are very dependent on pH so that e.g. in a basic environment at a pH from 8 to 10.5 they display predominantly esterase or amidase activity and at a pH from 9 to 10.5 no or only insignificant peptidase activity. These properties can be advantageously used in the process of the invention because they contribute to the achievement of good yields.

Further, it has been found that the ability to form said acyl enzyme intermediates are particularly pronounced in serine or thiol proteases. A preferred group of carboxypeptidases is therefore serine or thiol carboxypeptidases. Such enzymes can be produced by yeast fungi, or they may be of animal vegetable or microbial origin.

A particularly expedient enzyme is carboxypeptidase Y from yeast fungi (CPD-Y). This enzyme is described by Hayashi et al. (ref. 5) and by Johansen et al. (ref. 6) who developed a particularly expedient purification method by affinity chromatography on an affinity resin comprising a polymeric resin matrix with coupled benzylsuccinyl groups. CPD-Y, which is a serine enzyme, is characterized by having the above relation between the different enzymatic activities at pH>9 and by having no endopeptidase activity. In addition to its specificity for C-terminal amino acids or esters with free α-carboxyl groups, CPD-Y can also hydrolyze peptides in which the C-terminal α-carboxyl group is blocked in the form of an ester group, e.g. an alkyl or aryl ester or as an amide group or an N-substituted amide, e.g. an anilide. Importantly, the enzyme hydrolyzes most substrates, independent of the type of the C-terminal amino acid residue. Another advantage of CPD-Y is that it is available in large amounts and displays relatively great stability.

In addition to CPD-Y, which is the preferred enzyme at present, the process of the invention is feasible with other carboxypeptidases, such as those listed in the following survey:

| Enzyme | Origin |
| --- | --- |
| | Fungi |
| Penicillocarboxypeptidase S-1 | Penicillium janthinellum |
| Penicillocarboxypeptidase S-2 | Penicillium janthinellum |
| Carboxypeptidase(s) from | Aspergillus saitoi |
| Carboxypeptidase(s) from | Aspergillus oryzae |
| | Plants |
| Carboxypeptidase(s) C | Orange leaves |
| | Orange peels |
| Carboxypeptidase $C_N$ | Citrus natsudaidai Hayata |
| Phaseolain | French bean leaves |
| Carboxypeptidase(s) from | Germinating barley |
| | Germinating cotton plants |
| | Tomatoes |
| | Watermelons |
| | Bromelain pineapple powder |

Bovine carboxypeptidases A and B (CPD-A and CPD-B), however, are not suitable because they are metallocarboxypeptidases.

As explained above, the synthesis is based on a reaction of a so-called substrate component also called acid component or donor, and containing the moiety A with a so-called amine component, also called nucleophile component or acceptor, and containing the moiety B thereby to form a peptide A—B.

The moiety A, which is an amino acid residue or a peptide residue, can, if desired, be N-terminal amino protected to avoid undesirable secondary reactions.

The need for amino protection diminishes with increasing chain length of the peptide residue and is essentially non existent when the peptide residue consists of three amino acids, depending, however, upon their type and sequence.

Examples of useful amino acids are aliphatic amino acids, such as monoamino monocarboxylic acids, e.g. Glycine (Gly), alanine (Ala), valine (Val), norvaline (Nva), leucine (Leu), isoleucine (iso-Leu), and norleucine (Nle), hydroxy amino acids, such as serine (Ser), threonine (Thr) and homoserine (homo-Ser), sulfur-containing amino acids, such as methionine (Met) or cystine (CysS) and Cysteine (CysH), monoamino dicarboxylic acids, such as aspartic acid (Asp), glutamic acid (Glu), asparagine (Asn) and glutamine (Gln), diaminomonocarboxylic acids, such as ornithine (Orn), lysine (Lys) and arginine (Arg), aromatic amino acids, such as phenylalanine (Phe) and tyrosine (Tyr), as well as heterocylic amino acids, such as histidine (His) and tryptophan (Trp).

As protective groups may be used the amino protective groups common within the peptide chemistry, such as benzoyl (Bz), acetyl (Ac) or tertiary alkoxycarbonyl groups, e.g. t-butyloxycarbonyl (BOC-), t-amyloxycarbonyl (t-AOC-), benzyloxycarbonyl (Z-), p-methoxybenzyloxycarbonyl (PMZ-), 3,5-dimethoxybenzyloxycarbonyl (Z(OMe)$_2$-), 2,4,6-trimethylbenzyloxycarbonyl (TMZ-), p-phenylazobenzyloxycarbonyl (PZ-), p-toluenesulfonyl (Tos-), o-nitrophenylsulfenyl (Nps-), or the like.

Preferred protective groups are benzyloxycarbonyl and t-butyloxycarbonyl since these derivatives are easy to produce, economic in use and easy to cleave again.

As stated above the substrate component may be selected from the group consisting of (a) amino acid esters, peptide esters and depsipeptides of the formula $$A—OR^1 \text{ or } A—SR^1$$

wherein A is as defined above and $R^1$ represents alkyl, aryl, aralkyl or an α-des-amino fragment of an amino acid residue, (b) optionally N-substituted amino acid amides and peptide amides of the formula $$A—NHR^2$$

wherein A is as defined above and $R^2$ represents hydrogen, alkyl, aryl or aralkyl, and (c) optionally N-terminal protected peptides of the formula $$A—X$$

wherein A is as defined above and X represents an amino acid.

In this context "alkyl" means straight chain or branched alkyl, preferably with 1 to 6 carbon atoms, e.g. methyl, ethyl, propyl, isopropyl, butyl, isobutyl, tert. butyl, amyl, hexyl and the like.

"Aryl" means phenyl, heterocyclic aryl, and the like.

"Aralkyl" means benzyl, phenethyl, and the like.

All of these groups may be substituted with substituents which are inert with relation to the enzyme, e.g. halo (fluoro, chloro, bromo, iodo), nitro, alkoxy (methoxy, ethoxy, etc.), or alkyl (methyl, ethyl, etc.), provided the amino acid residue or the peptide derivative is a substrate for the carboxypeptidase.

Thus in case of esters of the group $OR^1$ is preferably selected from among alkoxy groups, such as methoxy, ethoxy or t-butoxy, phenyloxy-, and benzyloxy-group. The groups may optionally be substituted with inert substituents, such as nitro groups (p-nitrobenzyloxy). Other groups may be used as well if the amino acid residue or the peptide derivative is a substrate for the carboxypeptidase. An example is the so-called depsipeptides where the C-terminal amino acid is linked via an ester bond instead of a peptide bond, e.g. benzoyl-glycin-phenyl lactate (Bz-Gly-OPhe).

Preferred carboxylic acid protective groups are alkoxy groups, in particular methoxy groups or, in other words: The substrate component preferably contains or consists of an amino acid methyl ester since these derivatives are easy to produce and good substrates at the same time. However, e.g. ethyl esters, propyl esters, isopropyl esters, butyl esters, t-butyl esters, benzyl esters or tert. butyloxy esters may be used equally well.

It should be mentioned that ionizable groups which may be present in the individual amino acids, which are constituents of a peptide residue A, may, if desired, be blocked in a manner known per se, depending upon the type of the group. However, this is not always required, which is precisely one of the advantages of the present process. If it is desired to protect the functional groups, suitable protective groups for the ω-amino group ($N^\omega$) are e.g. $N^\omega$-benzyloxycarbonyl ($N^\omega$—Z), t-butoxycarbonyl ($N^\omega$—BOC) or tosyl ($N^\omega$—Tos). Suitable protective groups for the N-guanidino group ($N^G$) in Arg are Nitro ($N^G$—$NO_2$), $N^G$-benzyloxycarbonyl ($N^G$—Z) and $N^G,N^G$-dibenzyloxycarbonyl ($N^G$—Z—Z). Suitable protective groups for the imidazole ring ($N^{im}$) in His are $N^{im}$-benzyl ($N^{im}$—Bzl) and Tosyl ($N^{im}$—Tos).

Suitable protective groups for the ω-carboxyl groups are ω-benzyloxy (—OBzl). Suitable protective groups for the hydroxyl group in aliphatic or aromatic hydroxy amino acids are aralkyl groups, such as benzyl (Bzl). Suitable S-protective groups for the mercapto group in CysH are e.g. the benzyl group (Bzl). The protective groups must be stable during the primary reaction and be easy to cleave from the final product without causing any secondary reactions.

The process of the invention can in principle be carried out with any amino acid as substrate component.

The second participant in the reaction is the so-called amine component which is selected from the group consisting of (a) amino acids of the formula $$H—B—OH,$$

(b) optionally N-substituted amino acid amides of the formula $$H—B—NHR^3$$

wherein B is an amino acid residue and $R^3$ represents hydrogen, hydroxy, amino or alkyl, aryl or aralkyl, and (c) amino acid esters or thioesters of the formula $H—B—OR^4$ or $H—B—SR^4$, respectively wherein B is an amino acid residue and $R^4$ represents alkyl, aryl and aralkyl.

The alkyl, aryl and aralkyl groups may be substituted and are defined as explained in connection with the substrate component.

It is seen that $R^3$=hydrogen represents the free amide, while $R^3$=OH is a hydroxamic acid, $R^3$=amino is a hydrazide, and $R^3$=phenyl represents an anilide.

The process of the invention thus possesses the decisive advantage over e.g. Isowa and Morihara (op.cit.) that is can be carried out both with free (not C-terminal protected) amino acids, and with amino acids which are C-terminal protected e.g. by conversion into the corresponding amides, anilides, hydrazides, esters or other specified carboxyl derivatives of amino acids.

As regards the amine component, the reaction sequence, yields, etc. depend very much upon whether the components are introduced as free acid or as C-protected derivative, e.g. as amide. This will be illustrated in greater detail below in connection with the examples; the following general picture seems to emerge, however:

It applies to the free acids that the hydrophobic amino acids, such as alanine, leucine, valine and phenylalanine, as well as acids with a positively charged side chain, such as lysine and arginine, are relatively easy to incorporate in the chain of the substrate component, while amino acids whose side chains contain either carboxyl groups (aspartic acid or glutamic acid), hydroxyl groups (serine and threonine) or amide groups (asparagine and glutamine) are more difficult to incorporate.

Heterocyclic amino acids, such as proline and histidine, are extremely difficult to incorporate as free acids.

It is a different matter if C-terminal protected amino acids e.g. amino acid amides, or N-substituted amides, e.g. hydrazides or anilides are used as amine component. This will be elaborated below, but it may be said quite generally that in this case the reaction is highly independent of the structure and allows even very high yields (up to 90%) to be obtained; however, here too, heterocyclic amino acids are more difficult to incorporate than aliphatic ones.

As stated above, the process of the invention is carried at pH 5.0 to 10.5, preferably at pH 8.0 to 10.5. The preferred pH-value, which is often within a very narrow range, depends upon the pH-optima and pH-minima, respectively, for the different enzymatic activities of the enzyme used, it being understood that the pH-value should be selected so that the activities are counter-balanced as explained in the foregoing.

Generally, the peptidase activity increases with decreasing pH-values below about 9.0 thereby rendering the process less advantageous in terms of yield. However, in some cases, e.g. with Bz-Ala-Gly or Bz-Ala-Gly-NH$_2$, the formed peptides or peptide amides are very poor substrates for the carboxypeptidase, so that the esterase activity versus the amino acid ester or peptide ester preferably used as substrate component still dominates, thereby making a synthesis possible even at pH-values about or below 5.0. Generally speaking, the optimum pH depends on the actual starting materials, the formed peptides and the enzyme.

If CPD-Y is used as enzyme, the pH-value is preferably 8.0 to 10.5, particularly 9.0 to 10.5, as explained below.

This pH-value should be maintained throughout the coupling reaction, and may then be changed for precipitation of the reaction product, cleavage of protective groups, etc. This may be provided for by incorporating a suitable buffer for the selected pH-range in the reaction medium, such as a bicarbonate buffer.

However, the selected buffer is not critical to the reaction, provided the proper pH is maintained.

The pH-value may also be maintained by adding an acid, such as HCl, or a base, such as NaOH, during the reaction. The reaction is, as mentioned, carried out in an aqueous reaction medium which, if desired, may contain up to 50% of an organic solvent. Preferred organic solvents are alkanols, e.g. methanol and ethanol, glycols, e.g. ethylene glycol or polyethylene glycols, dimethyl formamide, dimethyl sulfoxide, tetrahydrofurane, dioxane and dimethoxyethane.

The selection of the composition of the reaction medium depends particularly upon the solubility, temperature and pH of the reaction components and the peptide product, and upon the stability of the enzyme.

The reaction medium may also comprise a component that renders the enzyme insoluble, but retains a considerable part of the enzyme activity, such as an ion exchanger resin. Alternatively the enzyme may be immobilized in known manner, cf. Methods of Enzymology, Vol. 44, 1976, e.g. by bonding to a matrix, such as a cross-linked dextran or agarose, or to a silica, polyamide or cellulose, or by encapsulating in polyacrylamide, alginates or fibres. Besides, the enzyme may be modified by chemical means to improve its stability or enzymatic properties.

The concentration of the two participants in the reaction may vary within wide limits, as explained below. A preferred starting concentration for the substrate component is 0.01 to 1 molar and for the amine component 0.05 to 3 molar.

The enzyme activity may vary as well, but is preferably $10^{-6}$ to $10^{-4}$ molar.

According to the invention the reaction temperature is preferably 20° to 50° C. The most appropriate reaction temperature for a given synthesis can be determined by experiments, but depends particularly upon the used amine component and enzyme. An appropriate temperature will usually be about 35° to 45° C., preferably about 35° C. At temperatures lower than 20° C. the reaction time will usually be inappropriately long, while temperatures above 50° C. often cause problems with the stability of the enzyme and/or reactants or of the reaction products.

Similar variations occur for the reaction time which depends very much upon the other reaction parameters, as explained below. The standard reaction time in the process of the invention is about 10 minutes, but may take up to a few hours.

It should be added that when using an amide or substituted amide as the amine component, it is often advantageous or even necessary to cleave the amide group specifically from the formed peptide amide in order to continue the synthesis. Also in this respect the carboxypeptidase, especially CPD-Y is very suitable since as described above CPD-Y exhibits amidase activity at pH > 9 while the carboxypeptidase activity is negligible.

By the same token the carboxypeptidase might generally be used to cleave the groups $R^3$ or $R^4$ as defined from the formed peptide whether it is desired to continue the synthesis or just to obtain a final peptide which is not C-terminal protected.

As will be further illustrated below the process of the invention is applicable for the formation of an unlimited number of dipeptides, oligopeptides and polypeptides, based on the same inventive principle, viz. reacting a substrate component with an amine component in the form of an amino acid or amino acid derivative in the presence of a carboxypeptidase.

Examples of well-known oligopeptides or polypeptides which may be produced accordingly are enkephalins, somatostatin, somatostatin analogs and peptides with similar biological activities, and the so-called "sleep peptide" (Trp-Ala-Gly-Gly-Asp-Ala-Ser-Gly-Glu).

In certain cases, e.g. when dealing with peptides consisting of more than five amino acids, it might be advantageous to synthesize parts of the desired peptide in the form of oligopeptide fragments e.g. pentapeptides with the suitable amino acid sequences and subject the oligopeptides to fragment condensation in any manner known per se.

It might also be advantageous in order to improved e.g. the solubility characteristics of the peptide formed to use as the N-terminal amino acid arginine or another ionizable amino acid during the synthesis steps and then cleave the arginine from the peptide with a specific enzyme e.g. trypsin, when the desired amino acid sequence is otherwise in order.

These and other modifications also form part of the invention.

Before the process of the invention will be illustrated by examples, starting materials, methods of measurement, etc. will be explained in general terms.

STARTING MATERIALS

Carboxypeptidase Y from baker's yeast was isolated by the affinity chromatography procedure of Johansen et al. (ref. 6) and obtained as a lyophilized powder (10% enzyme in sodium citrate). Before use the enzyme was desalted on Sephadex ® G-25 fine (1.5×25 cm) equilibrated and eluted with distilled water. The concentration of the enzyme was determined spectrophotometrically using $E_{280}1\%$ nm=14.8 (ref. 6). A stock solution of 7 mg/ml (110 μM) was prepared and stored in aliquots of 250-500 μl at −21° C. Benzoylalanine methyl ester (Bz-Ala-OMe) was purchased from Bachem, Liestal, Switzerland. Boron trifluoride etherate complex (for synthesis), solvents and reagents (all analytical grade) were from Merck, Darmstadt, West Germany. All amino acids and amino acid amides and their derivatives were from Sigma Chemical Company, St. Louis, USA. Carbobenzyloxy-phenylalanine methyl ester (Z-Phe-OMe) was prepared according to the procedure of Yamada et al. (ref. 20) and used as a syrup. Phenylalanine hydrazide and alanine hydrazide hydrochloride were prepared from the esters as described by Losse et al. (ref. 11). The uncorrected melting points were 86°–88° C. (Lit.: 82°–83° C. (11)) and 182°–185° C. (Lit.: 184°–185° C. (21)), respectively. Asparagine amide dihydrochloride was obtained from aspartic acid via the diethyl ester according to Fischer (ref. 4) by classical aminolysis (m.p.: 210°–214° C., Lit.: 214°–215° C. (19)). Other starting materials were provided from the above companies or produced in analogous manner.

DETERMINATION OF PRODUCT YIELDS

The purity was determined qualitatively by TLC on Silica Gel 60 F$_{254}$ (Merck). The solvent system used was CHCl$_3$/CH$_3$(CH$_2$)$_3$OH/CH$_3$COOH/H$_2$O (11:5:2:1) and the spots were visualized by fluorescence quenching for estimation of the reactant composition.

The reactant compositions were determined quantitatively by reverse-phase HPLC using an RP-8, 10 μm (Merck) column and a Hewlett Packard 1084 Chromatograph equipped with a variable wavelength UV detector (Model 79875 A). Separation was achieved using suitable specific gradients of elution systems from 10% CH$_3$CN in 10 mM-NaAc, pH 4 to 100% CH$_3$CN or from 10 mM-NaAc, pH 4 to 100% CH$_3$CN. The latter system was used for compounds such as Bz-Ala-Gly-OH, Bz-Ala-Ala-OH, Bz-Ala-Ser-OH and their respective amides, cf. below. The flow rate was 3 ml/min, the column temperature 47° C. and the monitoring wavelength 260 nm. The yields were determined on the basis of the molar ratio of the reactants which was obtained from the integrated areas under the peaks in the elution profile.

IDENTIFICATION OF PRODUCTS

The spots were identified by thin-layer cochromatography with suitable standard compounds. Several products were identified by a combination of HPLC and amino acid analysis. For this purpose, 1 ml-aliquots were taken from the reaction mixture after 10 minutes, and the reaction was discontinued by adding 250 μl 6 M-HCl. The pH was then adjusted to 4 with NaOH and the mixture separated by HPLC using Waters equipment including two pumps, a Model 660 Solvent Programmer, a Model U6K Injector, a Model 450 Variable Wavelength Detector combined with a Recorder (Radiometer REC 61) or a Hewlett Packard Recorder/Integrator Model 3380A. Elution was monitored by scanning at a suitable wavelength between 255-280 nm. The chromatography was reverse-phase using a Waters C-18 μ-Bondapak column with the elution system TEAP-20% (v/v) TEAP (trimethylammoniumphosphate buffer) in methanol under suitable gradients and flow rates of 1.5–2.0 ml/min. The TEAP-buffer was prepared according to Rivier (ref. 17). In many cases the system 0.1 M-HAc, pH 3–20% (v/v) 0.1 M-HAc, pH3 in methanol gave also sufficient resolution.

The effluent containing the N-acyldipeptides were collected manually and taken to dryness by lyophilization or on a Büchi Rotovap at 35°-45° C. Small samples of the residues were hydrolyzed in 6 M-HCl at 110° C. in vacuo for 36 h. The evaporated hydrolyzates were then analysed on a Durrum D-500 amino acid analyzer.

SYNTHESIS WITH FREE AMINO ACIDS AS AMINE COMPONENT

Example 1

A solution of 2 ml of 0.6M Valine-0.1M KCl-1 mM EDTA, pH 9.8 was mixed with 100 μl (0.1 mmole) of a 1M Bz-Ala-OMe (dissolved in 96% ethanol) solution. The reaction was carried out in a pH-stat at 35° C. and pH 9.8, the pH-value being kept constant by automatic addition of 0.5M NaOH. The reaction was initiated by adding 0.7 mg of carboxypeptidase Y (150 U/mg, prepared by De Forenede Bryggerier). After a reaction time of 30 minutes, the reaction was discontinued by adjusting pH to about pH=1 with 6M HCl. The reaction product was purified and isolated by means of high pressure chromatography. The yield of Bz-Ala-Val-OH was 40%. Quantitative amino acid analysis after hydrolysis of the product in 6M HCl for 24 hours gave relatively 1.0 mole of Alanine and 1.0 mole of Valine.

The effect of pH, temperature and concentration of substrate component, amine component and CPD-Y on the yield in the above reaction:

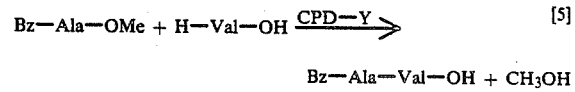

$$Bz-Ala-OMe + H-Val-OH \xrightarrow{CPD-Y}$$ [5]

$$Bz-Ala-Val-OH + CH_3OH$$

was studied in five separate series of experiments analogously with the above-mentioned procedure. One of the parameters mentioned below was varied in each experiment, while the four others were kept constant: 0.6M valine, 55 mM Bz-Ala-OMe, 4.5 mM CPD-Y, pH 9.7, 35° C. The results are shown in FIG. 1. It will be seen from FIG. 1A that the pH-range for optimal yield is rather narrow, extending over 0.5 pH units only. It will be seen from FIG. 1B that an increase in the reaction temperature caused an almost linear increase of synthesis on account of relatively less hydrolysis. At temperatures above 45° C., enzyme inactivation and non-enzymatic ester hydrolysis became prohibitive. At lower temperatures and pH-values up to 10.0, the ester hydrolysis was negligible within the 10 minutes standard reaction time. It became significant, however, when the enzymatic reaction rate was inhibited and called for reaction times up to 2 to 5 hours.

While the yields of Bz-Ala-Val-OH increased with higher amine component concentration (FIG. 1D), the reverse was the case for the relationship between yield and concentration of the substrate component Bz-Ala-OMe (FIG. 1C). The latter observation, taken together with the dependency of yield on high enzyme concentration (FIG. 1E), suggests an optimal ratio of substrate to enzyme concentrations.

Figure 2:
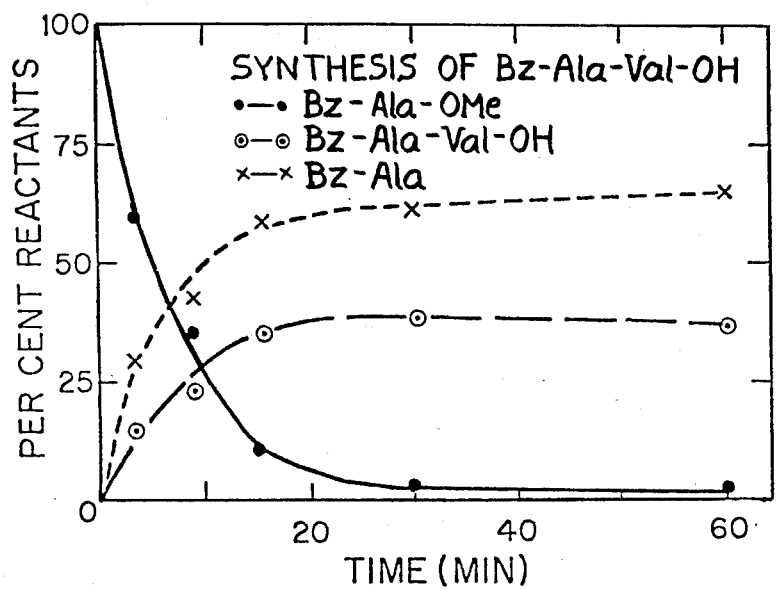

The time course of a typical reaction, illustrated by the above reaction under conditions little short of optimum is illustrated in FIG. 2. In the presence of 0.5M valine, the substrate Bz-Ala-OMe was rapidly converted (within 20 minutes) to 38% Bz-Ala-Val-OH and 62% Bz-Ala-OH. The figure also shows that the dipeptide was not hydrolyzed at pH 9.7 in the presence of excess valine. If, however, pH was adjusted to 5 to 8, all Bz-Ala-Val-OH was hydrolyzed within seconds. This selective behaviour of CPD-Y at high pH is an important property for its usefulness in peptide syntheses.

als stated. The experiments were carried out in a Radiometer pH-stat and the yields were determined by HPCL (cf. the foregoing). The conditions were 4.5 μM CPD-Y; pH 9.7 and 35° C.

TABLE I

Carboxypeptidase-Y catalyzed synthesis of peptides with free amino acids as amine component.

| Substrate (conc.) | Amine component (concentration) | Product | Yield % |
|---|---|---|---|
| Bz—Ala—OMe (55 mM) | Glycine (3.0 M) | Bz—Ala—Gly—OH | 62 |
| | Alanine (1.9 M) | Bz—Ala—Ala—OH | 65 |
| | Valine (0.6 M) | Bz—Ala—Val—OH (Ex. 1) | 40 |
| | Leucine (0.17 M) | Bz—Ala—Leu—OH | 24 |
| | Phenylalanine (0.16 M) | Bz—Ala—Phe—OH | 27 |
| | Serine (3.2 M) | Bz—Ala—Ser—OH | 50 |
| | Threonine (0.7 M) | Bz—Ala—Thr—OH | 24 |
| | Methionine (0.6 M) | Bz—Ala—Met—OH | 46 |
| | Lysine (1.5 M) | Bz—Ala—Lys—OH | 56 |
| | Arginine (0.8 M) | Bz—Ala—Arg—OH | 26 |
| | Aspartic acid (1.0 M) | Bz—Ala—Asp—OH | 0 |
| | Asparagine (0.6 M) | Bz—Ala—Asn—OH | 5 |
| | Glutamic acid (1.2 M) | Bz—Ala—Glu—OH | 0 |
| | Glutamic acid-γ-methyl ester (1.0 M) | Bz—Ala—Glu(OMe)—OH | 30 |
| Z—Phe—OMe (55 mM) | Valine (0.6 M) | Z—Phe—Val—OH | 6 |
| | Lysine (3.0 M) | Z—Phe—Lys—OH (Ex. 2) | 60 |
| Bz—Phe—Gly—OMe (30 mM) | Valine (0.6 M) | Bz—Phe—Gly—Val—OH | 40 |
| Z—Ala—OMe (10 mM) | Glycine (2.0 M) | Z—Ala—Gly—OH | 30 |
| | Alanine (0.7 M) | Z—Ala—Ala—OH | 60 |
| | Leucine (0.15 M) | Z—Ala—Leu—OH | 21 |
| | Lysine (1.5 M) | Z—Ala—Lys—OH | 60 |
| Bz—Gly—OMe (20 mM) | Glycine (2.0 M) | Bz—Gly—Gly—OH | 63 |
| | Leucine (0.15 M) | Bz—Gly—Leu—OH | 21 |
| Bz—Tyr—OEt (25 mM) | Valine (0.6 M) | Bz—Tyr—Val—OH | 30 |
| | Alanine (1.9 M) | Bz—Tyr—Ala—OH | 46 |
| | Arginine (0.8 M) | Bz—Tyr—Arg—OH | 35 |
| Ac—Phe—OEt (50 mM) | Alanine (0.8 M) | Ac—Phe—Ala—OH | 85 |
| Z—Ala—Ala—OMe (10 mM) | Glycine (2.0 M) | Z—Ala—Ala—Gly—OH | 40 |
| | Leucine (0.15 M) | Z—Ala—Ala—Leu—OH | 0 |
| | Phenylalanine (0.15 M) | Z—Ala—Ala—Phe—OH | 0 |
| Z—Ala—Phe—OMe (10 mM) | Glycine (2.0 M) | Z—Ala—Phe—Gly—OH | 35 |
| | Leucine (0.15 M) | Z—Ala—Phe—Leu—OH | 0 |
| Z—Ala—Ser—OMe (10 mM) | Leucine (0.15 M) | Z—Ala—Ser—Leu—OH | 40 |
| Z—Ala—Val—OMe (10 mM) | Leucine (0.15 M) | Z—Ala—Val—Leu—OH | 25 |
| | Lysine (1.5 M) | Z—Alu—Val—Lys—OH | 60 |
| Z—Ala—NLeu—OMe (10 mM) | Glycine (2.0 M) | Z—Ala—NLeu—Gly—OH | 60 |
| | Leucine (0.15 M) | Z—Ala—NLeu—Leu—OH | 16 |
| Z—Ala—Met—OMe (10 mM) | Glycine (2.0 M) | Z—Ala—Met—Gly—OH | 50 |
| | Leucine (0.15 M) | Z—Ala—Met—Leu—OH | 15 |
| Z—Ala—Trp—OMe (10 mM) | Glycine (2.0 M) | Z—Ala—Trp—Gly—OH | 23 |
| | Leucine (0.15 M) | Z—Ala—Trp—Leu—OH | 3 |
| Z—Ala—Trp—OMe (10 mM) | Phenylalanine (0.15 M) | Z—Ala—Trp—Phe—OH | 0 |
| | Lysine (1.5 M) | Z—Ala—Trp—Lys—OH | 36 |
| Z—Ala—Ala—Tyr—OMe (10 mM) | Leucine (0.15 M) | Z—Ala—Ala—Tyr—Leu—OH | 0 |
| | Lysine (1.5 M) | Z—Ala—Ala—Tyr—Lys—OH | 23 |
| | Alanine (1.7 M) | Z—Ala—Ala—Tyr—Ala—OH | 31 |

Example 2

A solution of 2 ml of 3M lysine-0.1M KCl-1 mM EDTA, pH 9.8 was mixed with 400 μl of 100% methanol and 100 μl (0.1 mmole) of a 1M Z-Phe-OMe (dissolved in 100% methanol). The reaction was carried out as described in example 1 and initiated by adding 0.7 mg of carboxypeptidase-Y. After a reaction time of 30 minutes, pH was adjusted to 1 with 6M HCl. The reaction product was purified and isolated by means of high pressure chromatography. The yield of Z-Phe-Lys-OH was 60%. Quantitative amino acid analysis, as described in example 1, showed that the product relatively contained 1.0 mole of lysine and 1.0 mole of phenylalanine.

Analogously with examples 1 and 2, the peptides listed in table I were prepared from the starting materi-

SYNTHESIS WITH AMINO ACID AMIDES AS AMINE COMPONENT

Example 3

A solution of 2 ml of 0.6M methionine amide (Met—NH₂)-0.1M KCl-1 mM EDTA, pH 9.8, was mixed with 100 μl (0.1 mmole) of a 1M Bz-Ala-OMe solution in 96% methanol. The reaction was carried out as described in example 1 and initiated by adding 0.7 mg of carboxypeptidase-Y. After a reaction time of 30 minutes, pH was adjusted to 1 with 6M HCl. The reaction product was purified and isolated by means of high pressure chromatography. The yield of Bz-Ala-Met-NH₂ was 95%. Quantitative amino acid analysis, as described in example 1, showed that the product relatively contained 1.0 mole of Ala, 1.0 mole of Met and 1.0 mole of NH₃.

Figure 3:
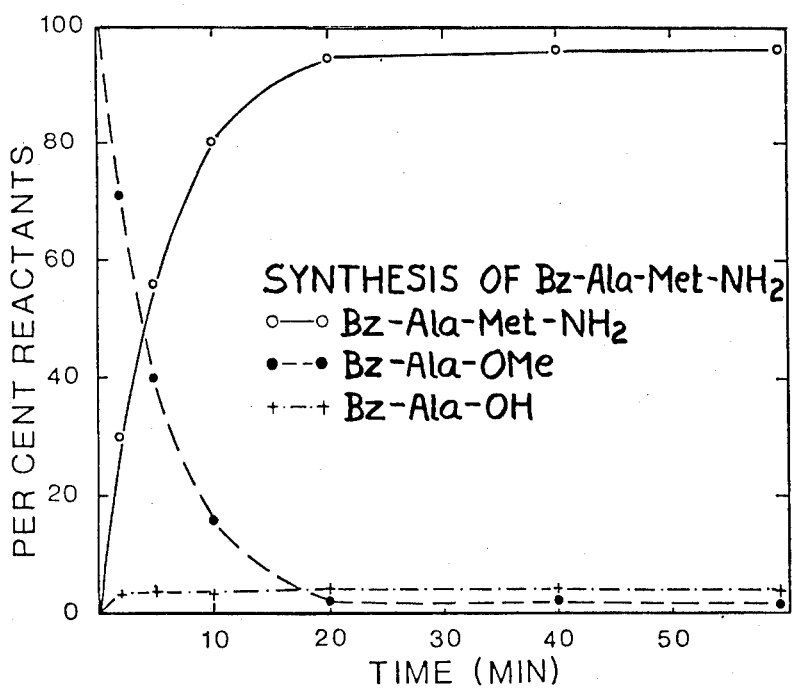

The course for the reaction is shown in FIG. 3, from which it appears that within 20 minutes the substrate is converted almost completely to about 95% dipeptide, 5% being hydrolyzed to Bz-Ala-OH.

Example 4

A solution of 2 ml of 0.4M valine amide (Val-NH₂)- 0.1M KCl-1 mM EDTA, pH 9.5, was mixed with 100 μl (0.1 mmole) of a 1M Bz-Ala-OMe solution in 96% ethanol. The reaction was carried out as described in example 1. The reaction product Bz-Ala-Val-NH₂ precipitated during the reaction. After 20 minutes' reaction pH was adjusted to 1, and the precipitate was isolated by centrifugation. The product was dissolved in 1 ml of 96% ethanol and purified and isolated by high pressure chromatography. The yield of Bz-Ala-Val-NH₂ was 95%, while, as shown in example 1, it was only 40% when the free acid was used as amine component. Quantitative amino acid analysis, as described in example 1, showed that the product relatively contained 1.0 mole of Ala, 1.0 mole of Val and 1.0 mole of NH₃.

Figure 4:
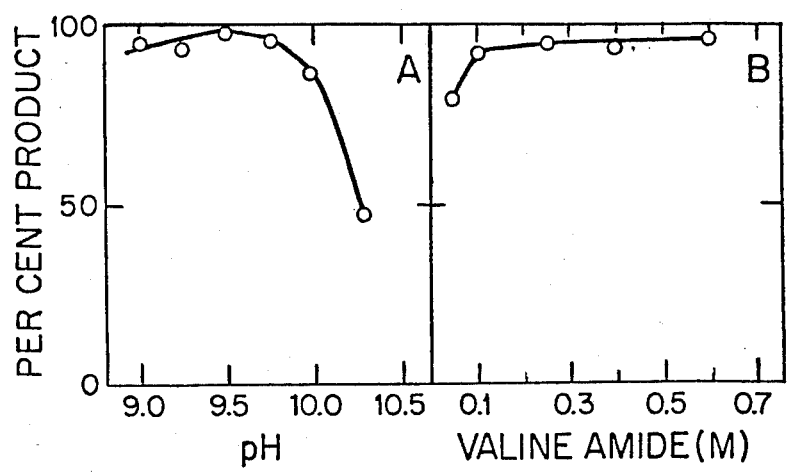

The dependency of the reaction sequence on pH and the valine amide concentration is shown in FIG. 4. The reaction was carried out analogously with the synthesis above, the constant parameters being: Valine amide 0.6M, Bz-Ala-OMe 55 mM, CPD-Y 4.5 μM, pH 9.7, 35° C.

It will be seen from FIG. 4B that the yield is essentially insensitive to the variation in the valine amide concentration in contrast to FIG. 1D which shows the yield with varying valine concentration, at least a concentration equimolar to or higher than the substrate concentration (55 mM).

It will be seen from FIG. 4A that the effective pH-range of valine amide extends down to 9.0, there being a sharp upper limit at pH 9.8 above which the yield decreases heavily.

Analogously with examples 3 and 4, the peptides listed in table II were prepared from the starting materials stated. The experiments were carried out under the following conditions: 4.5 μM CPD-Y; pH 9.6 and 35° C., while the substrate concentration is stated in the table.

TABLE II

Carboxypeptidase-Y catalyzed synthesis of peptides with amino acid amides as amino component.

| Substrate (conc.) | Amine component (concentration) | Product | Yield % |
|---|---|---|---|
| Bz—Ala—OMe (55 mM) | Glycine amide (0.3 M) | Bz—Ala—Gly—NH₂ | 90 |
| | Serine amide (0.3 M) | Bz—Ala—Ser—NH₂ | 90 |
| | Valine amide (0.4 M) (Ex. 4) | Bz—Ala—Val—NH₂ | 95[b] |
| | Leucine amide (0.3 M) | Bz—Ala—Leu—NH₂ | 85 |
| | Methionine amide (0.6 M) (Ex. 3) | Bz—Ala—Met—NH₂ | 95 |
| | Phenylalanine amide (0.3 M) | Bz—Ala—Phe—NH₂ | 90[b] |
| | Tyrosine amide (0.6 M) | Bz—Ala—Tyr—NH₂ | 90 |
| | Asparagine amide (0.3 M) | Bz—Ala—Asn—NH₂ | 80 |
| | Proline amide (0.3 M) | Bz—Ala—Pro—NH₂ | 0 |
| | Glutamic acid amide (0.25 M) | Bz—Ala—Glu—NH₂ | 0 |
| | Histidine amide (0.2 M) | Bz—Ala—His—NH₂ | 89 |
| | Threonine amide (0.2 M) | Bz—Ala—Thr—NH₂ | 88 |
| Z—Phe—OMe (55 mM) | Valine amide (0.5 M) | Z—Phe—Val—NH₂ | 97[b] |
| | Serine amide (0.4 M) | Z—Phe—Ser—NH₂ | 60 |
| | Tyrosine amide (0.4 M) | Z—Phe—Tyr—NH₂ | 64 |
| Bz—Phe—Gly—OMe (30 mM) | Valine amide (0.4 M) | Bz—Phe—Gly—Val—NH₂ | 90 |
| Z—Phe—Ala—OMe (20 mM) | Valine amide (0.4 M) | Z—Phe—Ala—Val—NH₂ | 90[b] |
| | Glycine amide (0.4 M) | Z—Phe—Ala—Gly—NH₂ | 95 |
| | Histidine amide (0.4 M) | Z—Phe—Ala—His—NH₂ | 50 |
| Z—Leu—Gly—Gly—OEt | Valine amide (0.4 M) | Z—Leu—Gly—Gly—Val—NH₂ | 80 |
| Bz—Tyr—OEt (50 mM) | Valine amide (0.25 M) | Bz—Tyr—Val—NH₂ | 94 |
| | Glycine amide (0.55 M) | Bz—Tyr—Gly—NH₂ | 82 |
| Z—Ala—OMe (10 mM) | Leucine amide (0.15 M) | Z—Ala—Leu—NH₂ | 90 |
| | Glycine amide (0.15 M) | Z—Ala—Gly—NH₂ | 20 |
| Bz—Arg—OEt (75 mM) | Tyrosine amide (0.2 M) | Bz—Arg—Tyr—NH₂ | 52 |
| Bz—Tyr—OEt (50 mM) | Valine amide (0.25 M) | Bz—Tyr—Val—NH₂ | 94 |
| | Glycine amide (0.55 M) | Bz—Tyr—Gly—NH₂ | 82 |
| Z—Pro—OMe (50 mM) | Leucine amide (0.25 M) | Z—Pro—Leu—NH₂ | 0 |
| Bz—Gly—OMe (100 mM) | Histidine amide (0.2 M) | Bz—Gly—His—NH₂ | 20 |
| | Glycine amide (0.55 M) | Bz—Gly—Gly—NH₂ | 95 |
| | Leucine amide (0.25 M) | Bz—Gly—Leu—NH₂ | 95 |
| Z—Ala—Phe—OMe (10 mM) | Leucine amide (0.15 M) | Z—Ala—Phe—Leu—NH₂ | 95 |
| | Glycine amide (0.15 M) | Z—Ala—Phe—Gly—NH₂ | 84 |
| Z—Ala—Ala—OMe (10 mM) | Glycine amide (0.15 M) | Z—Ala—Ala—Gly—NH₂ | 100 |
| | Leucine amide (0.15 M) | Z—Ala—Ala—Leu—NH₂ | 100 |
| Z—Ala—Ser—OMe (10 mM) | Leucine amide (0.15 M) | Z—Ala—Ser—Leu—NH₂ | 95 |
| | Glycine amide (0.15 M) | Z—Ala—Ser—Gly—NH₂ | 70 |
| Z—Ala—Val—OMe (10 mM) | Leucine amide (0.15 M) | Z—Ala—Val—Leu—NH₂ | 84 |
| | Glycine amide (0.15 M) | Z—Ala—Val—Gly—NH₂ | 100 |
| Z—Ala—NLeu—OMe (10 mM) | Leucine amide (0.15 M) | Z—Ala NLeu—Leu—NH₂ | 100 |
| | Glycine amide (0.15 M) | Z—Ala—NLeu—Gly—NH₂ | 100 |

TABLE II-continued

Carboxypeptidase-Y catalyzed synthesis of peptides with amino acid amides as amino component.

| Substrate (conc.) | Amine component (concentration) | Product | Yield % |
|---|---|---|---|
| Z—Ala—Met—OMe (10 mM) | Glycine amide (0.15 M) | Z—Ala—Met—Gly—NH$_2$ | 95 |
| Z—Ala—Trp—OMe (10 mM) | Glycine amide (0.15 M) | Z—Ala—Trp—Gly—NH$_2$ | 84 |
|  | Leucine amide (0.15 M) | Z—Ala—Trp—Leu—NH$_2$ | 89 |
| Z—Thr—Pro—OMe (25 mM) | Valine amide (0.2 M) | Z—Thr—Pro—Val—NH$_2$ | 95 |
| Z—Ala—Ala—Tyr—OMe (10 mM) | Glycine amide (0.15 M) | Z—Ala—Ala—Tyr—Gly—NH$_2$ | 100 |
|  | Leucine amide (0.15 M) | Z—Ala—Ala—Tyr—Leu—NH$_2$ | 100 |
| Z—Tyr—Gly—Gly—OMe (20 mM) | Phenylalanine amide (0.2 M) | Z—Tyr—Gly—Gly—Phe—NH$_2$ | 40 |

[b]Product precipitated

Example 5

Synthesis with amino acid hydrazides as amine component

Analogously with examples 3 and 4 the peptides listed in Table III were prepared from the starting materials stated. The experiments were carried out under the following conditions: 4.5 μM CPD-Y, pH 9.6 and 35° C.

TABLE III

Carboxypeptidase-Y catalyzed synthesis of peptides with amino acid hydrazides as amine component

| Substrate (conc.) | Amine component (concentration) | Product | Yield % |
|---|---|---|---|
| Bz—Ala—OMe (55 mM) | Alanine-hydrazide (0.6 M) | Bz—Ala—Ala—NH—NH$_2$ | 37 |
|  | Phenylalanine hydrazide (0.3 M) | Bz—Ala—Phe—NH—NH$_2$ | 80 |

Example 6

Synthesis with amino acid esters as amine component

The experiments with amino acid esters were carried out analogously with examples 1, 2, 3 and 4, in a Radiometer pH-stat at pH 9.0–9.7 and 23°–35° C. Products and yields were determined by HPLC. The CPD-Y concentration was from 4.5 to 11 μM.

Table IV states the peptides produced from the mentioned starting materials.

It is seen that in some cases a certain oligomerization is obtained. Since the yields generally are very high, amino acid esters appear to be extremely useful if oligomerization can be further limited.

TABLE IV

Carboxypeptidase-Y catalyzed synthesis of peptides with amino acid esters as amine component.

| Substrate (conc.) | Amine component (concentration) | Product | Yield % |
|---|---|---|---|
| Bz—Ala—OMe (50 mM) | Glycine ethyl ester (0.5 M) | Bz—Ala—Gly—OH<br>Bz—Ala—Gly—Gly—OH | 100 |
|  | Glycine propyl ester (0.5 M) | Bz—Alu—Gly—OH | 85 |
|  | Glycine isopropyl ester (0.5 M) | Bz—Ala—Gly—OH | 90 |
|  | Glycine butyl ester (0.5 M) | Bz—Ala—Gly—OH | 80 |
|  | Leucine methyl ester (0.25 M) | Bz—Ala—Leu—OH<br>Bz—Ala—Leu—Leu—OH<br>Bz—Ala—Leu—Leu—Leu—OH<br>Bz—Ala—Leu—Leu—Leu—Leu—OH | 85 |
|  | Leucine ethyl ester (0.25 M) | Bz—Ala—Leu—OH<br>Bz—Ala—Leu—Leu—OH | 50 |
|  | Leucine-t-butyl ester (0.25 M) | Bz—Ala—Leu—OH | 0 |
|  | Phenylalanine methyl ester (0.25 M) | Bz—Ala—Phe—OH<br>Bz—Ala—Phe—Phe—OH<br>Bz—Ala—Phe—Phe—Phe—OH | 80 |
| Bz—Ala—OMe (50 mM) | Phenylalanine ethyl ester (0.15 M) | Bz—Ala—Phe—OH<br>Bz—Ala—Phe—Phe—OH | 70 |
|  | Glutamic acid (γ-t-Bu) methyl ester (0.5 M) | Bz—Ala—Glu (γ-t-Bu)—OH | 35 |

TABLE IV-continued

Carboxypeptidase-Y catalyzed synthesis of peptides with amino acid esters as amine component.

| Substrate (conc.) | Amine component (concentration) | Product | Yield % |
|---|---|---|---|
| | Glutamic acid (γ-t-Bu) t-butyl ester (0.25 M) | Bz—Ala—Glu (γ-t-Bu)—OH | 0 |
| | Methionine methyl ester (0.2 M) | Bz—Ala—Met—OH<br>Bz—Ala—Met—Met—OH<br>Bz—Ala—Met—Met—Met—OH<br>Bz—Ala—Met—Met—Met—Met—OH<br>Bz—Ala—Met—Met—Met—Met—Met—OH | 86 |
| | Methionine ethyl ester (0.2 M) | Bz—Ala—Met—OH | 40 |
| | Methionine isopropyl ester (0.2 M) | Bz—Ala—Met—OH | 8 |
| | Valine methyl ester (0.7 M) | Bz—Ala—Val—OH<br>Bz—Ala—Val—Val—OH | 85 |
| | Serine methyl ester (0.5 M) | Bz—Ala—Ser—OH | 50 |
| | Tyrosine methyl ester (0.5 M) | Bz—Ala—Tyr—OH | 25 |
| | Arginine methyl ester (0.5 M) | Bz—Ala—Arg—OH | 0 |
| | Arginine (NO$_2$) methyl ester (0.5 M) | Bz—Ala—Arg(NO$_2$)—OH | 40 |
| | Histidine methyl ester (0.5 M) | Bz—Ala—His—OH | 26 |
| | Threonine methyl ester (0.5 M) | Bz—Ala—Thr—OH | 47 |
| Ac—Phe—OEt (50 mM) | Alanine methyl ester (0.5 M) | Ac—Phe—Ala—OH<br>Ac—Phe—Ala—Ala—OH | 60 |
| Bz—Gly—OMe (50 mM) | Histidine methyl ester (0.5 M) | Bz—Gly—His—OH | 40 |

Example 7

L- and D-stereoisomers of the amino component

Analogously with examples 1, 2, 3, 4, and 6, the peptides stated in Table V were produced from the listed starting materials.

It is seen that only the L-isomers are incorporated. This is a very interesting feature in terms of process economy since it is consequently not necessary to purify the starting amino acids with a view to obtain the pure L-isomer.

TABLE V

Carboxypeptidase-Y catalyzed synthesis of peptides with L- and D-isomers of the amine component.

| Substrate (conc.) | Amine component (concentration) | Product | Yield % L-isomer | Yield % D-isomer |
|---|---|---|---|---|
| Bz—Ala—OMe (50 mM) | Valine (0.6 M) | Bz—Ala—Val—OH | 42 | 0 |
| | Alanine (1.8 M) | Bz—Ala—Ala—OH | 65 | 0 |
| Bz—Tyr—OEt (30 mM) | Valine (0.6 M) | Bz—Tyr—Val—OH | 30 | 0 |
| | Alanine (1.8 M) | Bz—Tyr—Ala—OH | 46 | 0 |
| Bz—Ala—OMe (50 mM) | Val—NH$_2$ (0.25 M) | Bz—Ala—Val—NH$_2$ | 78 | 0 |
| Bz—Tyr—OEt (30 mM) | Val—NH$_2$ (0.25 M) | Bz—Tyr—Val—NH$_2$ | 95 | 0 |
| Ac—Phe—OEt (50 mM) | Ala—OMe (0.5 M) | Ac—Phe—Ala—OH<br>Ac—Phe—(Ala)$_2$—OH | 60 | 0 |

Example 8

Variation of the substrate ester group

Analogously with examples 1, 2, 3, and 4 the peptides stated in Table VI were produced from the listed starting materials.

The results prove the flexibility of the process of the invention as regards applicable substrates.

TABLE VI

Yield (%) of carboxypeptidase-Y catalyzed synthesis of peptides with different ester groups on the substrate component.

| Amine component | Substrate | | | |
|---|---|---|---|---|
| | Bz—Gly—OMe (20 mM) | Bz—Gly—OEt (20 mM) | Bz—Gly—OiPr (20 mM) | Bz—Gly—OBz (20 mM) |
| Glycine (2.0 M) | 63 | 56 | 45 | 47 |
| Glycine amide (0.15 M) | 59 | 95 | 88 | 91 |
| Leucine | 21 | 59 | 74 | 80 |

TABLE VI-continued

Yield (%) of carboxypeptidase-Y catalyzed synthesis of peptides with different ester groups on the substrate component.

| Amine component | Substrate | | | |
|---|---|---|---|---|
| | Bz—Gly—OMe (20 mM) | Bz—Gly—OEt (20 mM) | Bz—Gly—OiPr (20 mM) | Bz—Gly—OBz (20 mM) |
| (0.15 M) | | | | |
| Leucine amide (0.15 M) | 95 | 100 | 95 | 95 |

Example 9

Depsipeptides as substrates

Analogously with examples 3 and 4 the peptides stated in Table VII were produced from the listed starting materials. The conditions were 4.5 $\mu$M CPD-Y, pH=7.6 and 25° C.

It is seen that very high yields are obtained.

TABLE VII

Carboxypeptidase-Y catalyzed synthesis of peptides with depsipeptides as substrate components.

| Substrate (conc.) | Amine component (concentration) | Product | Yield % |
|---|---|---|---|
| Bz—Gly—OGly (20 mM) | Glycine amide (0.25 M) | Bz—Gly—Gly—NH$_2$ | 90 |
| | Leucine amide (0.25 M) | Bz—Gly—Leu—NH$_2$ | 95 |
| | Phenylalanine amide (0.25 M) | Bz—Gly—Phe—NH$_2$ | 95 |
| Bz—Gly—OPhe (20 mM) | Glycine amide (0.25 M) | Bz—Gly—Gly—NH$_2$ | 95 |
| | Leucine amide (0.25 M) | Bz—Gly—Leu—NH$_2$ | 95 |
| | Phenylalanine amide (0.25 M) | Bz—Gly—Phe—NH$_2$ | 95 |
| Bz—Phe—OGly (20 mM) | Glycine amide (0.25 M) | Bz—Phe—Gly—NH$_2$ | 90 |
| | Leucine amide (0.25 M) | Bz—Phe—Leu—NH$_2$ | 80 |
| | Phenylalanine amide (0.25 M) | Bz—Phe—Phe—NH$_2$ | 80 |

Example 10

Peptides as substrate components

Analogously with examples 1, 2, 3, and 4 the peptides stated in Table VIII were produced. The experiments were carried out in a Radiometer pH-stat and the yields determined by HPLC. The conditions were 5 $\mu$M CPD-Y, pH=7.6 and 25° C.

TABLE VIII

Carboxypeptidase-Y catalyzed synthesis of peptides with peptides as substrates.

| Substrate (conc.) | Amine component (concentration) | Product | Yield % |
|---|---|---|---|
| Bz—Phe—Gly (20 mM) | Leucine amide (0.25 M) | Bz—Phe—Leu—NH$_2$ | 90 |
| Bz—Gly—Phe (20 mM) | Leucine amide (0.25 M) | Bz—Gly—Leu—NH$_2$ | 10 |
| Z—Ala—Ala (20 mM) | Leucine amide (0.25 M) | Z—Ala—Leu—NH$_2$ | 74 |
| Z—Phe—Ala (20 mM) | Leucine amide (0.25 M) | Z—Phe—Leu—NH$_2$ | 60 |
| Z—Phe—Ser (20 mM) | Leucine amide (0.25 M) | Z—Phe—Leu—NH$_2$ | 70 |

Peptide synthesis as a function of pH

In cases where the synthesized peptide is a poor substrate for CPD-Y the synthesis may be carried out at pH-values below the preferred 9–10.5.

Example 11

Analogously with examples 1 and 3 the peptides stated in Table IX were produced in a pH-stat at the listed pH-values.

The conditions were 15 $\mu$M CPD-Y and 25° C.

TABLE IX

Carboxypeptidase-Y catalyzed synthesis of peptides as a function of pH.

| Substrate (conc.) | Amine component (concentration) | Product | pH | Yield % |
|---|---|---|---|---|
| Bz—Ala—OMe (50 mM) | Glycine (1.3 M) | Bz—Ala—Gly | 9.5 | 40 |
| | | | 9.0 | 57 |
| | | | 8.0 | 60 |
| | | | 7.0 | 61 |
| | | | 6.0 | 60 |
| | | | 5.0 | 51 |
| | Glycine amide (1.3 M) | Bz—Ala—Gly—NH$_2$ | 9.5 | 77 |
| | | | 9.0 | 95 |
| | | | 8.0 | 100 |
| | | | 7.0 | 97 |
| | | | 6.0 | 44 |

VARIOUS OTHER AMINE COMPONENTS

Example 12

Analogously with examples 3 and 4 the peptides stated in Table X were produced. The experiments were carried out in a pH-stat and the yields determined by HPLC. The conditions were 4.5 $\mu$M CPD-Y, pH 9.7 and 25° C.

TABLE X

Carboxypeptidase-Y catalyzed synthesis of peptides with different amino acid derivatives as amine components.

| Substrate (conc.) | Amine component (concentration) | Product | Yield % |
|---|---|---|---|
| Bz—Ala—OMe (50 mM) | β-alanine amide (0.2 M) | Bz—Ala—βAla—NH$_2$ | 80 |
| | Glycine hydroxamic acid (0.2 M) | Bz—Ala—Gly—NH—OH | 45 |
| | D,L-Alanine hydroxamic acid (0.2 M) | Bz—Ala—Ala—NH—OH | 40 |

Example 13

Synthesis of peptides with carboxypeptidases from barley

Germinating barley, e.g. in the form of malt, contains two different peptidases denominated CP-1-1 and CP-2-1 (see Lee E. Ray, Carlsberg Res. Comm. 41, 169–182 (1976)).

CP-1-1 and CP-2-1 were isolated as described by L. E. Ray and the peptides listed in Table XI were produced analogously with examples 1, 2, 3, and 4 from the listed starting materials. The conditions were 6 μM CP-1-1 or CP-2-1, pH 8.0 and 25° C.

TABLE XI

Synthesis of peptides using carboxypeptidases from germinating barley CP-1-1 and CP-2-1.

| Substrate (conc.) | Amine component (concentration) | Product | Yield % | Enzyme |
|---|---|---|---|---|
| Bz—Ala—OMe (50 mM) | Valine amide (0.25 M) | Bz—Ala—Val—NH$_2$ | 43 | CP-1-1 |
| | Alanine amide (0.25 M) | Bz—Ala—Ala—NH$_2$ | 58 | CP-1-1 |
| | Lysine (1.7 M) | Bz—Ala—Lys | 11 | CP-1-1 |
| | Valine amide (0.25 M) | Bz—Ala—Val—NH$_2$ | 57 | CP-2-1 |
| | Alanine amide (0.25 M) | Bz—Ala—Ala—NH$_2$ | 64 | CP-2-1 |
| | Lysine (1.7 M) | Bz—Ala—Lys | 11 | CP-2-1 |

Example 12

Carboxypeptidase-Y catalyzed deamidation of peptide amides

Figure 5:
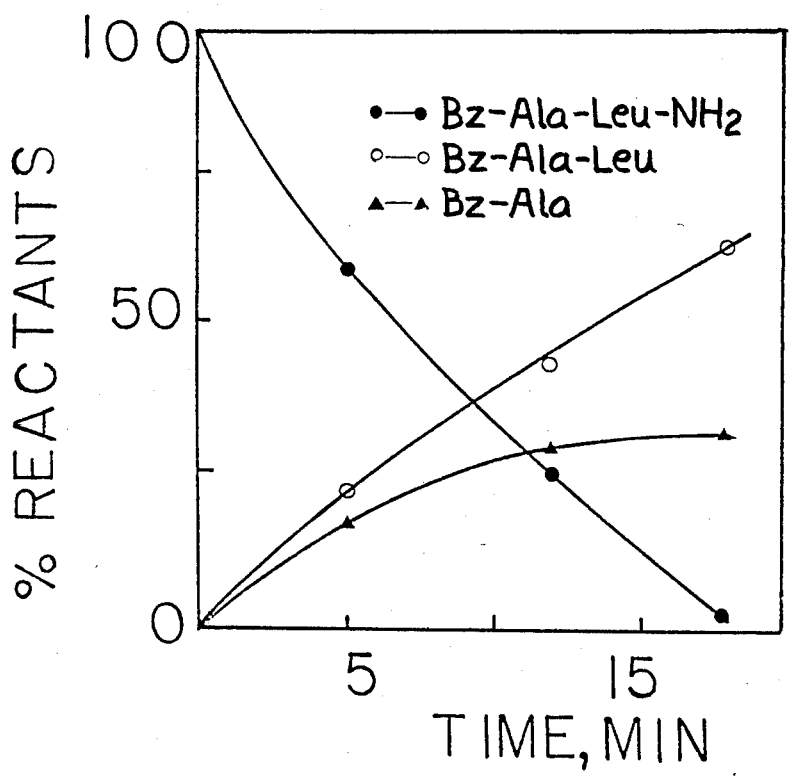

To a solution of 2 ml 15 mM Bz-Ala-Leu-NH$_2$ in 0.1M KCl-1 mM EDTA, pH 9.7, 25° C. and 10% dimethyl formamide was added 2 mg CPD-Y. The reaction course as shown on FIG. 5 was followed by HPLC as described in example 1. It is seen that Bz-Ala-Leu-NH$_2$ after 20 minutes was completely converted to about 68% Bz-Ala-Leu-OH and 32% Bz-Ala-OH. Amino acid analysis on the reaction mixture showed that the Bz-Ala-OH was mainly formed by cleavage of Leu-NH$_2$ from Bz-Ala-Leu-NH$_2$.

Example 13

Comparison of peptide ester substrates with and without N-terminal protective groups Analogously with examples 3 and 4 the peptides stated in Table XII were produced under the following conditions: 50 mM substrate, 5 μM CPD-Y, pH 9.5 and 25° C.

TABLE XII

Comparison of carboxypeptidase-Y catalyzed synthesis of peptides using peptide esters with and without N-terminal protective groups as substrate.

| Substrate (conc.) | Amine component (concentration) | P Product | Yield % |
|---|---|---|---|
| Ac—Ala—Ala—Ala—OMe (50 mM) | Leucine amide (0.15 M) | Ac—Ala—Ala—Ala—Leu—NH$_2$ | 90 |
| Ala—Ala—Ala—OMe (50 mM) | Leucine amide (0.15 M) | Ala—Ala—Ala—Leu—NH$_2$ | 75 |

Example 14

Synthesis in the presence of organic solvents

Analogously with examples 1, 2, 3, 4, and 6 the peptides stated in the below Tables XIII, XIV and XV were produced from the listed starting materials and with the listed concentrations of organic solvents.

The conditions were: 50 mM substrate, 5 μM CPD-Y, pH 9.6 and 30° C.

TABLE XIII

Carboxypeptidase-Y catalyzed synthesis of peptides with 50 mM Bz—Ala—OMe as substrate and free amino acids as amine component with and without 20% methanol (MeOH) in 0.1 M KCl, 1 mM EDTA.

| Amine component (concentration) | Product | Yield % without MeOH | Yield % with MeOH |
|---|---|---|---|
| Valine (0.6 M) | Bz—Ala—Val—OH | 42 | 53 |
| Threonine (1.2 M) | Bz—Ala—Thr—OH | 52 | 61 |
| Phenylalanine (0.16 M) | Bz—Ala—Phe—OH | 16 | 18 |
| Leucine (0.16 M) | Bz—Ala—Leu—OH | 33 | 39 |
| Methionine (0.6 M) | Bz—Ala—Met—OH | 42 | 64 |

TABLE XIII-continued

Carboxypeptidase-Y catalyzed synthesis of peptides with 50 mM Bz—Ala—OMe as substrate and free amino acids as amine component with and without 20% methanol (MeOH) in 0.1 M KCl, 1 mM EDTA.

| Amine component (concentration) | Product | Yield % without MeOH | Yield % with MeOH |
| --- | --- | --- | --- |
| Glycine (3.0 M) | Bz—Ala—Gly—OH | 55 | 50 |
| Serine (3.2 M) | Bz—Ala—Ser—OH | 50 | 52 |
| Lysine (1.5 M) | Bz—Ala—Lys—OH | 53 | 41 |
| Glutamic acid γ-t-butylester (1.0 M) | Bz—Ala—Glu (γ-OBu$^t$)—OH | 54 | 55 |
| Asparagin (0.6 M) | Bz—Ala—Asn—OH | 18 | 14 |

TABLE XIV

Carboxypeptidase-Y catalyzed synthesis of Bz—Ala—Thr—OH from Bz—Ala—OMe (50 mM) and threonine with varying concentrations of polyethylene glycol-300 (PEG-300). Conditions: CPD-Y 4 μM, pH 9.6 and 25° C.

| % PEG-300 in 0.1 M KCl | Threonine concentration | % Yield of Bz—Ala—Thr—OH |
| --- | --- | --- |
| 0 | 0.7 M | 36 |
| 10 | 0.7 M | 34 |
| 20 | 0.7 M | 31 |
| 30 | 0.7 M | 29 |
| 40 | 0.35 M | 28 |

TABLE XV

Carboxypeptidase-Y catalyzed synthesis of peptides from 50 mM Bz—Ala—OMe and the listed amino acid esters as amine component in 30% polyethylene glycol-0.1 M KCl, 1 mM EDTA. The other conditions were: CPD-Y = 8 μM, pH 9.6 and 25° C.

| Substrate (conc.) | Amine component (concentration) | Product | Yield % |
| --- | --- | --- | --- |
| Bz—Ala—OMe (50 mM) | Valine-OMe (0.5 M) | Bz—Ala—Val—OH<br>Bz—Ala—Val—Val—OH | 88 |
| | Serine-OMe (0.5 M) | Bz—Ala—Ser OH | 30 |
| | Glutamic acid (γ-OBu$^t$)—OMe (0.5 M) | Bz—Ala Glu—(γ-OBu$^t$)—OH | 38 |
| | Phenylalanine-OMe (0.5 M) | Bz—Ala—Phe—OH<br>Bz—Ala—Phe—Phe—OH | 82 |
| Bz—Ala—OMe (50 mM) | L-Methionine-OMe (0.5 M) | Bz—Ala—Met—OH<br>Bz—Ala—Met—Met—OH<br>Bz—Ala—Met—Met—Met—OH | 85 |
| | D-Methionine-OMe (0.5 M) | Bz—Ala—D-Met—OH | 0 |

TABLE XVI

Insoluble carboxypeptidase-Y catalyzed synthesis of peptides.

| Substrate (conc.) | Amine component (concentration) | Product | Yield % |
| --- | --- | --- | --- |
| Bz—Ala—OMe (50 mM) | Phenylalanine (0.15 M) | Bz—Ala—Phe | 21 |
| | Leucine amide (0.2 M) | Bz—Ala—Leu—NH$_2$ | 91 |

Example 15

Insoluble (immobilized) carboxypeptidase-Y

CPD-Y was bonded to Concanavalin A-Sepharose 4B (Pharmacia Fine Chemicals) followed by cross-linking between CPD-Y and Concanavalin A with glutaraldehyde as described by Hsiao and Royer (Archives of Biochemistry and Biophysics, Vol. 198, 379–385 (1979). The CPD-Y concentration was 3 mg per ml packed Sepharose.

Analogously with examples 1 and 3 the peptides stated in Table XVI were produced under the following conditions: 50 mM substrate, 0.25 ml CPD-Y gel (5 μM CPD-Y), pH 9.7 and 35° C. After removal of the enzyme by filtration the products and yields were determined by HPLC.

REFERENCES (1) Bergmann M. & H. Fraenkel-Conrat: The role of specificity in the enzymatic synthesis of proteins. J. Biol. Chem. 119, 707–720 (1937)

(2) Bergmann M. & J. S. Fruton: Some synthetic and hydrolytic experiments with chymotrypsin, J. Biol. Chem. 124, 321–329 (1938)

(3) Fastrez, J. & A. R. Fersht: Demonstration of the acyl-enzyme mechanism for the hydrolysis of peptides and anilides by chymotrypsin. Biochemistry 12, 2025–2034 (1973)

(4) Fischer E.: Ueber die Ester der Aminosäuren. Chem. Ber. 34, 433–454 (1901)

(5) Hayashi R., Y. Bai & T. Hata: Kinetic studies of carboxypeptidase Y. I. Kinetic parameters for the hydrolysis of synthetic substrates. J. Biochem. 77, 69–79 (1975)

(6) Johansen, J. T., K. Breddam & M. Ottesen: Isolation of carboxypeptidase Y by affinity chromatography. Carlsberg Res. Commun. 41, 1–14 (1976)

(7) Isowa Y., M. Ohmori, T. Ichikawa, H. Kurita, M. Sato & K. Mori: The synthesis of peptides by means of proteolytic enzymes. Bull. Chem. Soc. Japan 50, 2762–2765 (1977)

(8) Isowa Y., M. Ohmori, M. Sato & K. Mori: The enzymatic synthesis of protected valine-5 angiotensinII amide-1. Bull. Chem. Soc. Japan 50, 2766–2772 (1977)

(9) Isowa Y., T. Ichikawa & M. Ohmori: Peptide synthesis with proteinases. Fragment condensation of ZLeuGlnGlyOH or ZGlnGlyOH with HLeuValNH$_2$ using metalloproteinases. Bull. Chem. Soc. Japan 51, 271–276 (1978)

(10) Klibanov A. M., G. P. Samokhin, K. Martinek & J. V. Berezin: A new approach to preparative enzymatic synthesis. Biotech. Bioeng. 19, 1351-1361 (1977)
(11) Losse G., H.-J. Hebel & C. Kästner: Racematspaltung von Aminosäureamiden und hydraziden. J. Prak. Chemie, 4. Reihe, Band 8, 345-350 (1959)
(12) Luisi P. L., R. Saltman, D. Vlach & R. Guarnaccia: Co-oligopeptides of glycine and aromatic amino acids with variable distance between the aromatic residues. VIII. Enaymatic synthesis of N-protected dipeptide esters. J. Mol. Catalysis 2, 133-138 (1977)
(13) Morihara K. & T. Oka: α-chymotrypsin as the catalyst for peptide synthesis. Biochem. J. 163, 531-542 (1977)
(14) Oka T. & K. Morihara: Peptide bond synthesis catalyzed by α-chymotrypsin. J. Biochem. 84, 1277-1283 (1978)
(15) Oka T & K. Morihara: Trypsin as a catalyst for peptide synthesis. J. Biochem. 82, 1055-1062 (1977)
(16) Oka T. & K. Morihara: Protease as a catalyst for peptide synthesis: Synthesis in the absence of product precipitation. Symp. on Peptide Chemistry in Japan, Osaka, pp. 79-84 (1977).
(17) Rivier J. E.: Use of trialkyl ammonium phosphate (TAAP) buffers in reverse phase HPLC for high resolution and high recovery of peptides and proteins. J. Liq. Chrom. 1, 343-366 (1978)
(18) Saltman R., D. Vlach & P. L. Luisi: Co-oligopeptides of aromatic amino acids and glycine with variable distance between the aromatic residues. VII. Enzymatic synthesis of N-protected peptide amides. Biopolymers 16, 631-638 (1977)
(19) Smith E. L. & D. J. Spackman: Leucine aminopeptidase V. Activation specificity and mechanism of action. J. Biol. Chem. 212, 271-299 (1955)
(20) Yamada Y., N. Isono, A. Inui, T. Miyazama, S. Kuwata & H. Watanabe: Esterification of N-(benzyloxycarbonyl)amino acids and amino acids using $BF_3$-etherate as catalyst. Bull. Chem. Soc. Japan 51, 1897-1898 (1978)
(21) Zeller E. A. L. A. Blanksma & J. A. Carbon: Ueber die Wirkung von optisch aktiven Hydraziden auf die Diaminoxydase. Helv. Chim. Acta. 40, 257-260 (1957)

We claim:

1. A process for producing a peptide of the general formula

A—B wherein A represents an N-terminal protected amino acid residue or an optionally N-terminal protected peptide residue and B represents an optionally C-terminal protected L-amino acid residue, which comprises:
reacting a substrate component selected from the group consisting of
optionally N-terminal protected peptides of the formula

A—X wherein A is as defined above and X represents an amino acid
with an amine component selected from the group consisting of
(a) optionally N-substituted amino acid amides of the formula

H—B—$NHR^3$ wherein B is an L-amino acid residue and $R^3$ represents hydrogen, hydroxy, amino or alkyl, aryl or aralkyl, and
(b) amino acid esters of the formula

H—B—$OR^4$ wherein B is an L-amino acid residue and $R^4$ represents alkyl, aryl and aralkyl,
in the presence of an L-specific serine or thiol carboxypeptidase enzyme from yeast or of animal, vegetable, or microbial origin in an aqueous solution or dispersion having a pH from 5 to 10.5.

2. The process according to claim 1, wherein the carboxypeptidase enzyme used is carboxypeptidase Y from yeast.

3. The process according to claim 2, wherein a carboxypeptidase Y is used which has been purified by affinity chromatography on an affinity resin comprising a polymeric resin matrix with a plurality of coupled benzylsuccinyl groups.

4. The process according to claim 1, wherein the carboxypeptidase enzyme used is selected from the group consisting of penicillocarboxypeptidase S-1 and S-2 from *Penicillium janthinellum*, carboxypeptidases from *Aspergillus saitoi* or *Aspergillus oryzae*, carboxypeptidases C from orange leaves or orange peels, carboxypeptidase $C_N$ from *Citrus natsudaidai Hayata*, phaseolain from bean leaves, carboxypeptidases from germinating barley, germinating cotton plants, tomatoes, watermelons and Bromelein (pineapple) powder.

5. The process according to claim 1, wherein an immobilized carboxypeptidase enzyme is used.

6. The process according to claim 1, wherein an aqueous reaction solution containing from 0 to 50% of organic solvent is used.

7. The process according to claim 6, wherein the organic solvent used is selected from the group consisting of alkanols, dimethyl sulfoxide, dimethyl formamide, dioxane, tetrahydrofurane, dimethoxy ethane, ethylene glycol and polyethylene glycols.

8. The process according to claim 1, wherein after formation of a peptide containing a group $R^3$ or $R^4$ or an N-terminal protective group any such group is cleaved.

9. The process according to claim 8 wherein the cleaving is performed by means of the same L-specific serine or thiol carboxypeptidase enzyme as was used in the formation of the peptide.

10. A process for producing a peptide of the general formula

A—B wherein A represents an N-terminal protected amino acid residue or an optionally N-terminal protected peptide residue and B represents an optionally C-terminal protected L-amino acid residue, which comprises:
reacting a substrate component selected from the group consisting of optionally N-terminal protected peptides of the formula

A—X wherein A is an defined above and X represents an amino acid, with an amine component selected from the group consisting of optionally N-substituted amino acid amides of the formula

H—B—NHR³, wherein B is an L-amino acid residue, and R³ represents hydrogen, methyl, ethyl, propyl, or isopropyl,
in the presence of an L-specific serine or thiol carboxypeptidase enzyme from yeast or of animal, vegetable, or microbial origin in an aqueous solution or dispersion having a pH from 5 to 10.5.

11. The process of claim 10 wherein R³ represents methyl, ethyl, propyl, or isopropyl.

12. A process for producing a peptide of the general formula

A—B wherein A represents an N-terminal protected amino acid residue or an optionally N-terminal protected peptide residue and B represents an optionally C-terminal protected L-amino acid residue, which comprises:
reacting a substrate component selected from the group consisting of optionally N-terminal protected peptides of the formula

A—X wherein A is as defined above and X represents an amino acid,
with an amine component selected from the group consisting of amino acid esters of the formula

H—B—OR⁴, wherein B is an L-amino acid residue, and R⁴ represents methyl, ethyl, propyl, or isopropyl,
in the presence of an L-specific serine or thiol carboxypeptidase enzyme from yeast or of animal, vegetable, or microbial origin in an aqueous solution or dispersion having a pH from 5 to 10.5.

* * * * *

UNITED STATES PATENT AND TRADEMARK OFFICE
CERTIFICATE OF CORRECTION

PATENT NO. : 4,806,473

DATED : February 21, 1989

INVENTOR(S) : Jack T. Johansen and Fred Widmer

It is certified that error appears in the above-identified patent and that said Letters Patent is hereby corrected as shown below:

| | |
|---|---|
| Column 3, Line 53: | "all" should be --call-- |
| Column 7, Line 36: | Delete "of" after "esters" |
| Column 8, Line 39: | "is" should be --it-- |
| Column 10, Line 47: | "improved" should be --improve-- |
| Column 10, Line 48: | "peptide" should be --peptides-- |

Signed and Sealed this

Fifth Day of September, 1989

Attest:

DONALD J. QUIGG

Attesting Officer

Commissioner of Patents and Trademarks

UNITED STATES PATENT AND TRADEMARK OFFICE
CERTIFICATE OF CORRECTION

PATENT NO. : 4,806,473
DATED : February 21, 1989
INVENTOR(S) : Johansen et al.

It is certified that error appears in the above-identified patent and that said Letters Patent is hereby corrected as shown below:

Title page:

Add the name "Klaus Breddam, Copenhagen, Denmark" as one of the inventors.

Add the following to References Cited:

Martin et al., Carlsberg Res. Commun. Vol 42 pp. 99-102 (1977)
Bai et al., J. Biochem., Vol 77, pp. 81-88 (1975)
Bai et al., J. Biochem. Vol 78, pp. 617-626 (1975)

Signed and Sealed this

Tenth Day of July, 1990

*Attest:*

HARRY F. MANBECK, JR.

*Attesting Officer*  *Commissioner of Patents and Trademarks*

UNITED STATES PATENT AND TRADEMARK OFFICE
CERTIFICATE OF CORRECTION

PATENT NO. : 4,806,473

DATED : February 21, 1989

INVENTOR(S) : Johansen et al.

It is certified that error appears in the above-identified patent and that said Letters Patent is hereby corrected as shown below:

Title page, item [73]:

The name of the assigne should be "Carlsberg Biotechnology Ltd. A/S"

Signed and Sealed this

Eleventh Day of June, 1991

Attest:

HARRY F. MANBECK, JR.

Attesting Officer

Commissioner of Patents and Trademarks